US012746064B2

(12) United States Patent
Ahn

(10) Patent No.: US 12,746,064 B2
**(45) Date of Patent: *Sep. 29, 2026**

(54) SKIN PROCEDURE GUIDANCE AND FEEDBACK SYSTEM

(71) Applicant: Ga Ram Ahn, Seoul (KR)

(72) Inventor: Ga Ram Ahn, Seoul (KR)

( * ) Notice: Subject to any disclaimer, the term of this patent is extended or adjusted under 35 U.S.C. 154(b) by 308 days.

This patent is subject to a terminal disclaimer.

(21) Appl. No.: 18/561,229

(22) PCT Filed: Nov. 11, 2022

(86) PCT No.: PCT/KR2022/017759

§ 371 (c)(1),
(2) Date: Nov. 15, 2023

(87) PCT Pub. No.: WO2024/029663

PCT Pub. Date: Feb. 8, 2024

(65) Prior Publication Data

US 2025/0072965 A1 Mar. 6, 2025

(30) Foreign Application Priority Data

Aug. 4, 2022 (KR) ........................ 10-2022-0097351

(51) Int. Cl.
*A61B 18/20* (2006.01)
*A61B 17/00* (2006.01)
(Continued)

(52) U.S. Cl.
CPC ........... *A61B 18/203* (2013.01); *G16H 40/60* (2018.01); *A61B 2017/00057* (2013.01);
(Continued)

(58) Field of Classification Search
CPC ........ A61B 18/203; A61B 2017/00057; A61B 2018/0047; A61B 2018/00589;
(Continued)

(56) References Cited

U.S. PATENT DOCUMENTS 6,997,923 B2 * 2/2006 Anderson ................ A61N 7/02 606/17
10,531,917 B2 * 1/2020 Johnson ............. A61B 18/1815
(Continued)

FOREIGN PATENT DOCUMENTS

JP 2016-512783 A 5/2016
JP 2021-523765 A 9/2021
(Continued)

OTHER PUBLICATIONS

Delval, Christophe, "European Search Report for EP Application No. 22954118.0", Apr. 17, 2025, EPO, Germany.
(Continued)

*Primary Examiner* — Jonathan T Kuo
(74) *Attorney, Agent, or Firm* — Bridgeway IP Law Group, PLLC; Jihun Kim

(57) ABSTRACT

Provided is a skin procedure guidance and feedback system that derives displacements of points before and after formation of a coagulation spot at each point on the skin surface based on an energy-based medical device, and calculates and feeds back a minimum distance that prevents coagulation zones from overlapping when coagulation spots are generated several times based thereon, including a photographing unit that photographs skin before and after the procedure, a displacement calculator that derives landmark displacement data from landmark location data of the skin photographed by the photographing unit, and derives location data of a contraction center based on the landmark displacement data, a boundary deriver that derives a boundary of a contraction zone from the contraction center in the skin procedure, and a procedure feedback unit that takes result data derived by the boundary deriver as input to feed back optimal parameter information for the procedure.

18 Claims, 15 Drawing Sheets

(51) Int. Cl.
*A61B 18/00* (2006.01)
*A61B 90/00* (2016.01)
*G16H 40/60* (2018.01)

(52) U.S. Cl.
CPC ................. *A61B 2018/0047* (2013.01); *A61B 2018/00589* (2013.01); *A61B 2018/00642* (2013.01); *A61B 2018/00982* (2013.01); *A61B 2018/00994* (2013.01); *A61B 2090/061* (2016.02)

(58) Field of Classification Search
CPC A61B 2018/00642; A61B 2018/00982; A61B 2018/00994; A61B 2090/061; A61B 2018/00452; A61B 5/0077; A61B 5/1079; A61B 5/441; A61B 5/4836; A61B 5/4887; A61B 5/442; A61B 5/4848; G16H 40/60; G16H 30/20; G16H 30/40; G16H 40/63; A61N 5/0616; A61N 7/02; A61N 2007/0034; A61N 5/06–2005/073; G06T 7/66; G06T 7/0016; G06T 2207/30088; G06T 7/0012; G06T 7/60
See application file for complete search history.

(56) References Cited

U.S. PATENT DOCUMENTS

| | | | | |
|---|---|---|---|---|
| 2002/0161357 | A1* | 10/2002 | Anderson ............ | A61B 18/203 606/17 |
| 2004/0008523 | A1 | 1/2004 | Butler | |
| 2008/0097558 | A1* | 4/2008 | Eggers ............... | A61B 18/1477 607/101 |
| 2008/0125771 | A1* | 5/2008 | Lau ...................... | A61B 18/203 606/41 |
| 2012/0226268 | A1* | 9/2012 | Liu ...................... | A61N 5/0613 606/9 |
| 2013/0346050 | A1 | 12/2013 | Kim et al. | |
| 2015/0032092 | A1 | 1/2015 | Adanny | |
| 2017/0296268 | A1* | 10/2017 | Johnson ............. | A61B 18/1815 |
| 2019/0029592 | A1 | 1/2019 | Yao et al. | |
| 2019/0099159 | A1 | 4/2019 | Voigt et al. | |
| 2019/0380584 | A1 | 12/2019 | Grodzki et al. | |
| 2025/0090084 | A1* | 3/2025 | Ahn ....................... | A61B 5/441 |

FOREIGN PATENT DOCUMENTS

| | | | |
|---|---|---|---|
| KR | 10-2013-0143434 | A | 12/2013 |
| KR | 10-2015-0135776 | A | 12/2015 |
| KR | 10-2018-0115377 | A | 10/2018 |
| KR | 10-2018-0136475 | A | 12/2018 |
| KR | 10-2188612 | B1 | 12/2020 |
| WO | 2017/180877 | A2 | 10/2017 |

OTHER PUBLICATIONS

Chen, Junbo et al., “Camera-Based Peripheral Edema Measurement Using Machine Learning,” IEEE International Conference on Healthcare Informatics, 2018, 115-122 page, IEEE Computer Society, DOI: 10.1109/ICHI.2018.00020. USA.

* cited by examiner (CASE 2) WHEN PLURALITY OF COAGULATION SPOTS IS GENERATED AT THE SAME TIME
(Linear, simultaneous model)

SKIN PROCEDURE GUIDANCE AND FEEDBACK SYSTEM

TECHNICAL FIELD

The present invention relates to a skin procedure guidance and feedback system, and more particularly to a skin procedure guidance and feedback system configured to derive displacements of points before and after formation of a coagulation spot at each point on the skin surface based on an energy-based medical device, and to calculate and feed back a minimum distance that prevents coagulation zones from overlapping when coagulation spots are generated several times based thereon.

BACKGROUND ART

The number of consumers visiting dermatologists due to skin sagging and undergoing skin procedures, such as lifting procedures, has been continuously increasing since such skin procedures have relatively short recovery periods compared to plastic surgeries and effectively enable facial wrinkle lifting (that is, skin area contraction).

Here, an energy-based medical device for skin area contraction forms a coagulation zone on the reticular dermis around a target point. In more detail, the reticular dermis includes spiral collagen bundles, which are arranged in a direction parallel to the skin surface, and when each bundle is thermally coagulated, a spiral structure unwinds and becomes tangled to be shorter. When energy is applied to one point of a reticular dermis layer to form a coagulation spot, the reticular dermis layer within a range of coagulation around the point contracts in a direction toward the coagulation spot in a plane parallel to the skin surface. When several such coagulation spots are formed with a narrow range, immediate contraction of the skin area is observed. Therefore, the energy-based medical device uses this principle to induce a cosmetic effect by flattening the skin.

However, there is a limitation that the effect is not constant when the procedure is performed on actual patients. In other words, efficiency of planar contraction of the skin through induction of multiple dermal coagulation spots is not consistent, and thus the efficiency of linear plane contraction is reduced. In addition, there is the case where efficiency of linear plane contraction is reduced due to overlap between coagulation zones, and when temperature excessively rises (for example, to about 80 degrees Celsius), there is a risk of covalent bonds inside collagen molecules breaking down, causing dissolution thereof.

Therefore, in theory, for optimal plane contraction, there is need for technology for generating a coagulation spot so that adjacent contraction zones are in contact. However, at present, in this procedure, a distance between coagulation spots and output adjustment of the device depend on intuition of an operator, and thus there are limitations in terms of efficiency, reproducibility, and safety of the procedure. Further, since an aspect of skin contraction induced by formation of dermal coagulation spots varies depending on skin conditions of the patients and various factors, there is a problem that efficiency is not consistent every time the procedure is performed.

In addition, a distance between multiple coagulation spots in an energy-based medical device is arbitrarily fixed, and even when a procedure distance can be changed by changing a set value of the device or replacing a handpiece, a determination on usage of a distance value depends on experience and intuition of the operator. In addition, when adjustment of the distance between multiple coagulation spots is limited, efforts are made to increase contraction efficiency by adjusting output of the energy-based medical device. However, this adjustment is made intuitively, and thus there are limitations in terms of efficiency, reproducibility, safety, etc.

DISCLOSURE

Technical Problem

Therefore, the present invention has been made in view of the above problems, and it is an object of the present invention to provide a skin procedure guidance and feedback system configured to acquire skin surface information before and after formation of a dermal coagulation spot of the skin through an energy-based medical device, and provide feedback to optimize a minimum distance that prevents coagulation zones from overlapping and an output energy factor of the energy-based medical device.

Technical Solution

In accordance with the present invention, the above and other objects can be accomplished by the provision of a skin procedure guidance and feedback system including a photographing unit configured to photograph skin before and after a procedure by an energy-based medical device, a displacement calculator configured to derive landmark displacement data from landmark location data of the skin photographed by the photographing unit, and to derive location data of a contraction center O based on the landmark displacement data, a boundary deriver configured to derive a boundary of a contraction zone from the contraction center O in the skin procedure, and a procedure feedback unit configured to take result data derived by the boundary deriver as input to feed back optimal parameter information for the procedure.

The energy-based medical device may be configured to apply energy to one focus of the skin to cause a local temperature rise, thereby generating a contraction zone based on the one focus of the skin, and include high-frequency, laser, and high-intensity focused ultrasound (HIFU) devices.

The photographing unit may photograph a skin surface before the procedure and a skin surface after the procedure based on the energy-based medical device.

Landmarks of the skin may include dots or lines marked with pigment, and sweat glands, hair glands, sebaceous glands, pigmented lesions, moles, skin tumors, blood vessels, and wrinkle lines on a skin surface as reference points enabling tracking of positional change of a skin procedure target part before and after the procedure in the photographed images before and after the skin procedure through the energy-based medical device.

The displacement calculator may include a preprocessor configured to convert location data A of landmarks before the skin procedure on a skin surface in an image of the skin surface before the skin procedure into A[(i, j)ij], and to convert location data B of landmarks after the skin procedure on the skin surface in an image of the skin surface after the procedure into B[(i', j')ij], and a displacement data calculator configured to calculate, as the landmark displacement data D, a displacement vector reflecting a result of movement from location data before the skin procedure to location data after the procedure based on the landmark location data of the skin derived by the preprocessor.

The displacement data calculator may represent the landmark displacement data D as [(i'-i, j'-j)ij].

(Here, i' and j' are a row i' and a column j' of B[(i', j')ij], and i and j are a row i and a column j of A[(i, j)ij].)

The boundary deriver may include a graph deriver configured to derive a displacement graph of each point moving toward the contraction center O for each location on a straight line passing through, at an angle ⊖, the contraction center O corresponding to a location of a focus to which the energy-based medical device applies energy based on the landmark displacement data, and a boundary deriver configured to calculate a distance R from the contraction center O to the boundary of the contraction zone based on graph analysis result data derived by the graph deriver.

The graph deriver may set the location data of the contraction center O corresponding to a location of a focus to which the energy-based medical device applies energy based on the landmark displacement data D, the location data of the contraction center O may be a location of a point to which landmark points on a skin surface are commonly directed during skin coagulation according to the procedure, and a location of an intersection point of straight lines, which are obtained by points corresponding to respective elements (i, j)ij of location data A of landmarks before the skin procedure on the skin surface each directed in a direction of an element $\vec{\delta}$ ij vector of the landmark displacement data D, may be set to (io, jo).

The graph deriver may perform parallel translation by -io on an i-axis and -jo on a j-axis with respect to a contraction center O (io, jo, 0) in the skin procedure, and perform rotation by the angle ⊖ at which the contraction center O in the skin procedure is passed through on a k-axis, thereby deriving a graph of k with respect to i in an ik-plane (j=0).

The boundary deriver may be configured to derive a graph of a regression curve of a distance by which each point moves toward the contraction center O in the skin procedure for each location on a horizontal line (⊖=0) passing through the contraction center O in the skin procedure, and calculate a distance from the contraction center O to the boundary R of the contraction zone from the photographed image before the procedure based on a fact that the distance is close to a distance from the contraction center O to a point where a slope of a tangent becomes 0 on the regression curve.

The procedure feedback unit may include a simultaneous energy feedback unit configured to feed back a minimum distance D preventing coagulation zones from overlapping each other when coagulation spots are simultaneously generated through the energy-based medical device (simultaneous model).

When a size of the contraction zone derived by the boundary deriver is smaller than a fixed procedure distance of the energy-based medical device, the simultaneous energy feedback unit may feed back high output energy value information to the energy-based medical device so that output of the energy-based medical device is allowed to be increased.

When a size of the contraction zone derived by the boundary deriver is greater than a fixed procedure distance of the energy-based medical device, the simultaneous energy feedback unit may feed back low output energy value information to the energy-based medical device so that output of the energy-based medical device is allowed to be decreased.

The procedure feedback unit may include a sequential energy feedback unit configured to feed back a minimum distance D' that prevents coagulation zones in (N−1)th to Nth rounds from overlapping when coagulation spots on the skin are sequentially generated through the energy-based medical device (sequential model).

The sequential energy feedback unit may feed back a location of a coagulation spot to be generated in the Nth round based on a displacement graph derived by the boundary deriver and information on a size and shape of a contraction zone based on one coagulation spot generated in the (N−1)th round.

Advantageous Effects

According to the skin procedure guidance and feedback system described above:

First, it is possible to derive displacement of each point on a skin surface that contracts when one focal point of skin is treated using an energy-based medical device.

Second, it is possible to derive a location of a contraction center caused by the procedure based on photographs taken before and after the procedure.

Third, it is possible to quantitatively express an aspect of skin contraction by the procedure based on the derived data.

Fourth, it is possible to quantitatively express an aspect of skin contraction, which varies according to a patient undergoing the procedure and a part thereof and according to a type and output of the device, whenever the system is applied.

Fifth, it is possible to generate data necessary for deriving an optimal next procedure location or procedure output during the procedure based on mathematical calculation rather than intuition of the operator.

Sixth, it is possible to combine distribution information on a contraction aspect of skin in several parts in one procedure target to calculate and propose a two-dimensional (2D) arrangement and order of several procedure points for realizing a change to desired appearance through manipulation of a location of each point on the skin.

BEST MODE

Figure 1:
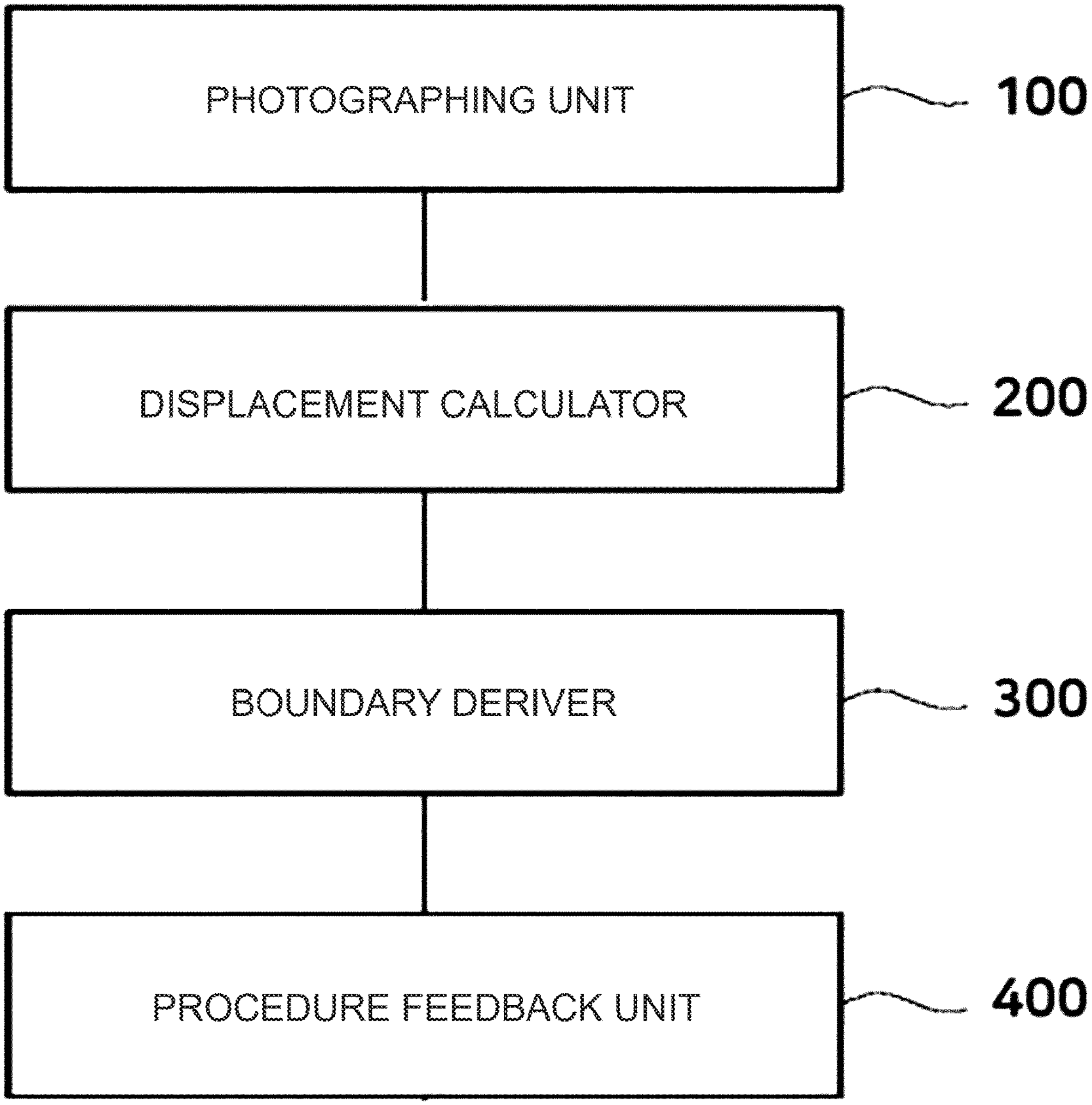
FIG. 1 is a configuration diagram of the present invention.

A skin procedure guidance and feedback system according to embodiments of the present invention will be described in detail with reference to the accompanying drawings. Since the present invention may undergo various changes and have various forms, specific embodiments will be illustrated in the drawings and described in detail in the text. However, this is not intended to limit the present invention to a specific form disclosed, and should be understood to include all modifications, equivalents, or substitutes included in the spirit and scope of the present invention. Like reference numerals have been used for like elements throughout the description of each figure. In the accompanying drawings, dimensions of structures are illustrated to be larger than actual ones for clarity of the present invention, or reduced compared to actual ones for understanding of schematic configurations.

In addition, even though terms such as first and second may be used to describe various components, the components should not be limited by the terms. The terms are only used for the purpose of distinguishing one component from another. For example, a first component may be referred to as a second component, and similarly, the second component may be may be referred to as the first component, without departing from the scope of the present invention. Meanwhile, unless defined otherwise, all terms used herein, including technical or scientific terms, have the same meaning as commonly understood by a person of ordinary skill in the art to which the present invention pertains. Terms such as those defined in commonly used dictionaries should be interpreted as having meanings consistent with meanings in the context of the related art, and should not be interpreted as having ideal or excessively formal meanings unless explicitly defined in the present application.

The present invention provides a skin procedure guidance and feedback system configured to acquire skin surface information before and after formation of a dermal coagulation spot of the skin through an energy-based medical device, and provide feedback to optimize a minimum distance that prevents coagulation zones from overlapping and an output energy factor of the energy-based medical device.

FIG. 1 is a configuration diagram of the present invention.

Referring to FIG. 1, a skin procedure guidance and feedback system includes a photographing unit 100, a displacement calculator 200, a boundary deriver 300, and a procedure feedback unit 400. The photographing unit 100 photographs the skin before and after a procedure by an energy-based medical device, and the displacement calculator 200 derives landmark displacement data from landmark location data of the skin photographed by the photographing unit 100, and derives location data of a contraction center O based on the landmark displacement data. The boundary deriver 300 derives a boundary of a contraction zone from the contraction center O in the skin procedure, and the procedure feedback unit 400 takes result data derived by the boundary deriver 300 as input to feed back optimal parameter information for the procedure.

Figure 2:
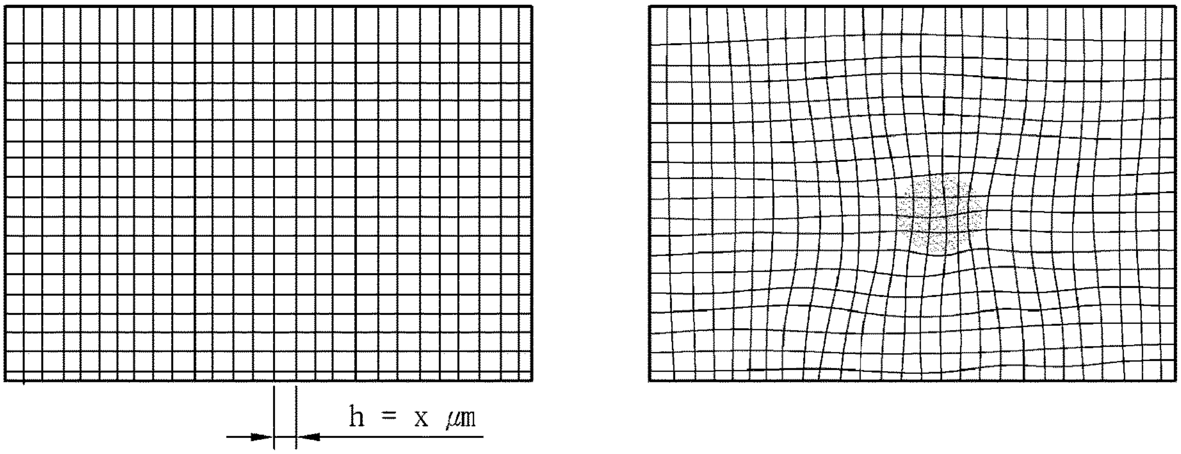
FIGS. 2 and 3 are schematic diagrams of skin landmarks, a helical structure diagram of collagen in skin, and exemplary views of contraction when a coagulation zone is generated in the skin.
Figure 3:
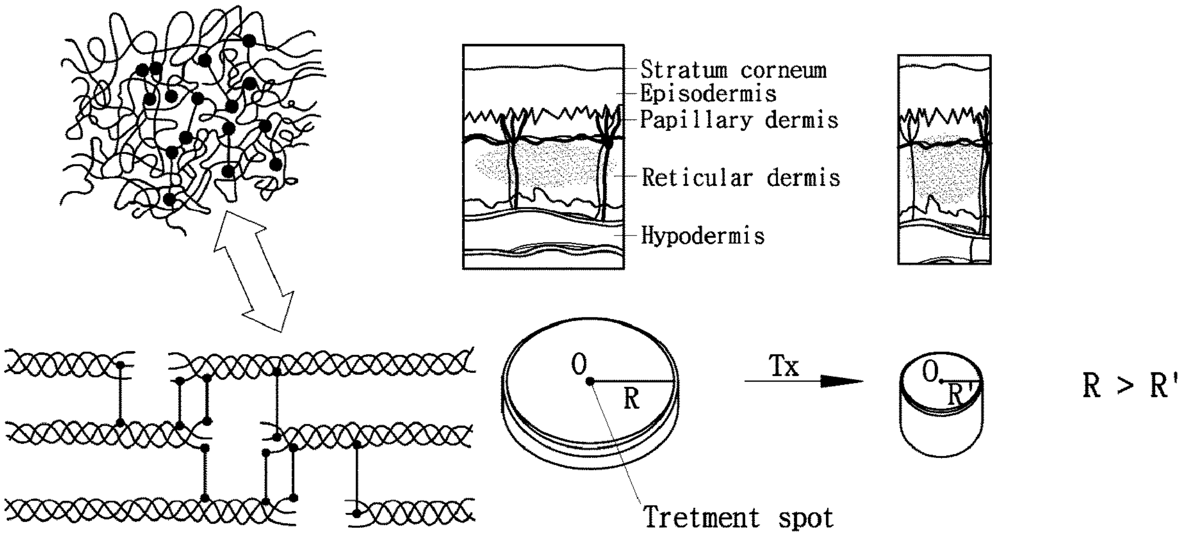

FIGS. 2 and 3 are schematic diagrams of skin landmarks, a helical structure diagram of collagen in skin, and exemplary views of contraction when a coagulation zone is generated in the skin.

Referring to FIG. 2, the skin landmarks are reference points enabling tracking of positional change of a skin procedure target part before and after the procedure in captured images before and after the skin procedure through the energy-based medical device, and include dots or lines marked with pigment, and sweat glands, hair glands, sebaceous glands, pigmented lesions, moles, skin tumors, blood vessels, and wrinkle lines on a skin surface. Referring to FIG. 3, there is a reticular dermis layer filled with collagen bundles in a deep layer of the skin surface. The reticular dermis layer includes spiral collagen bundles, and these collagen bundles are arranged in a direction parallel to the skin surface. When each of the bundles is thermally solidified, the bundle becomes shorter as a spiral structure unwinds and tangles. When a coagulation spot is formed by applying energy to one point of the reticular dermis layer, the reticular dermis layer within a range of coagulation around the point shrinks in a direction toward the corresponding coagulation spot in a plane parallel to the skin surface. Further, a contraction zone caused by one coagulation spot varies depending on several factors such as a patient undergoing the procedure, a part thereof, output of the device, a depth, and an angle.

Figure 4:
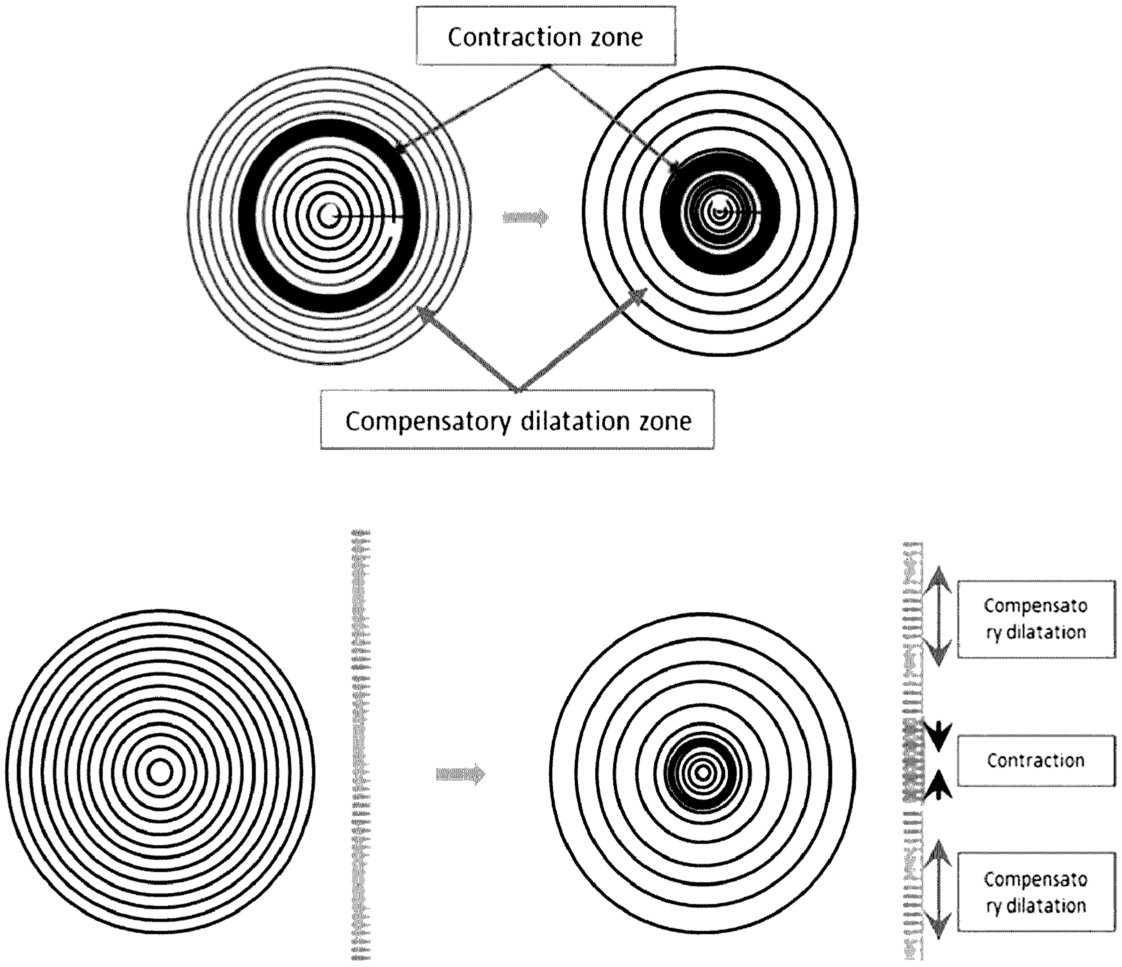
FIG. 4 is a schematic diagram of a skin contraction zone generated by a coagulation range of a reticular dermis layer of the skin when energy is irradiated to the skin using the energy-based medical device.

FIG. 4 is a schematic diagram of a skin contraction zone generated by a coagulation range of the reticular dermis layer of the skin when energy is irradiated to the skin using the energy-based medical device.

Referring to FIG. 4, when energy is applied to one focus of the reticular dermis by the energy-based medical device to form a coagulation spot, a contraction zone is formed within a distance R that may vary depending on the angle ⊖ based on the contraction center O. Within the contraction zone, each point on the skin surface moves toward the contraction center O, and as the density of the points increases, a distance between adjacent points becomes shorter. In addition, as the contraction zone is generated, the distance R from the contraction center O to the contraction zone boundary becomes shorter (R'<R). Conversely, at each point outside the distance R, that is, at a point outside the contraction zone, as the tension increases in a direction toward the contraction center O due to contraction generated within the contraction zone, a compensatory dilatation zone in which the density of each point on the skin surface is lowered is generated.

Figure 5:
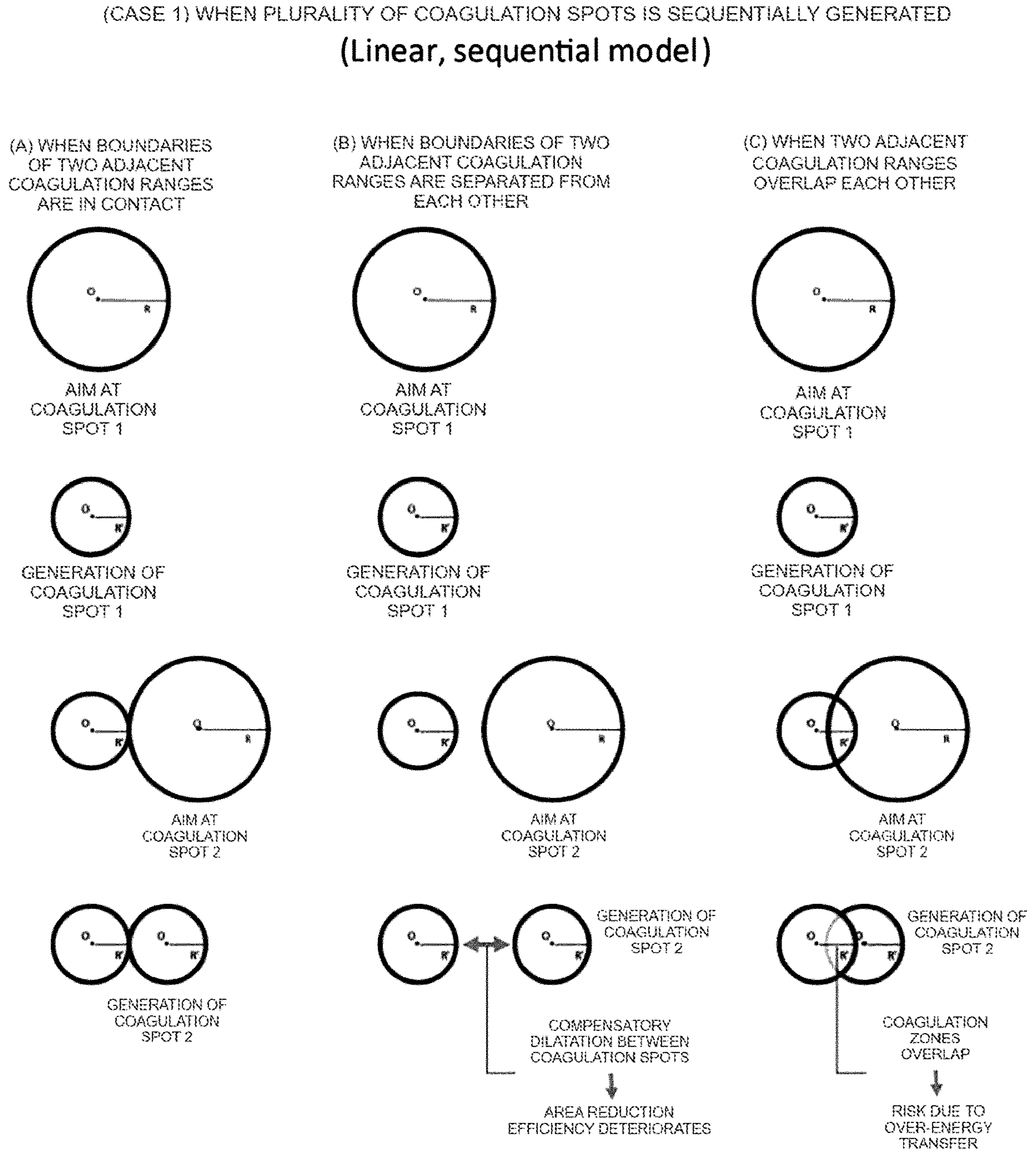
FIGS. 5 and 6 are diagrams describing that safety and area reduction efficiency may vary depending on the distance between adjacent coagulation spots when reducing the area of the skin by generating several coagulation spots.
Figure 6:
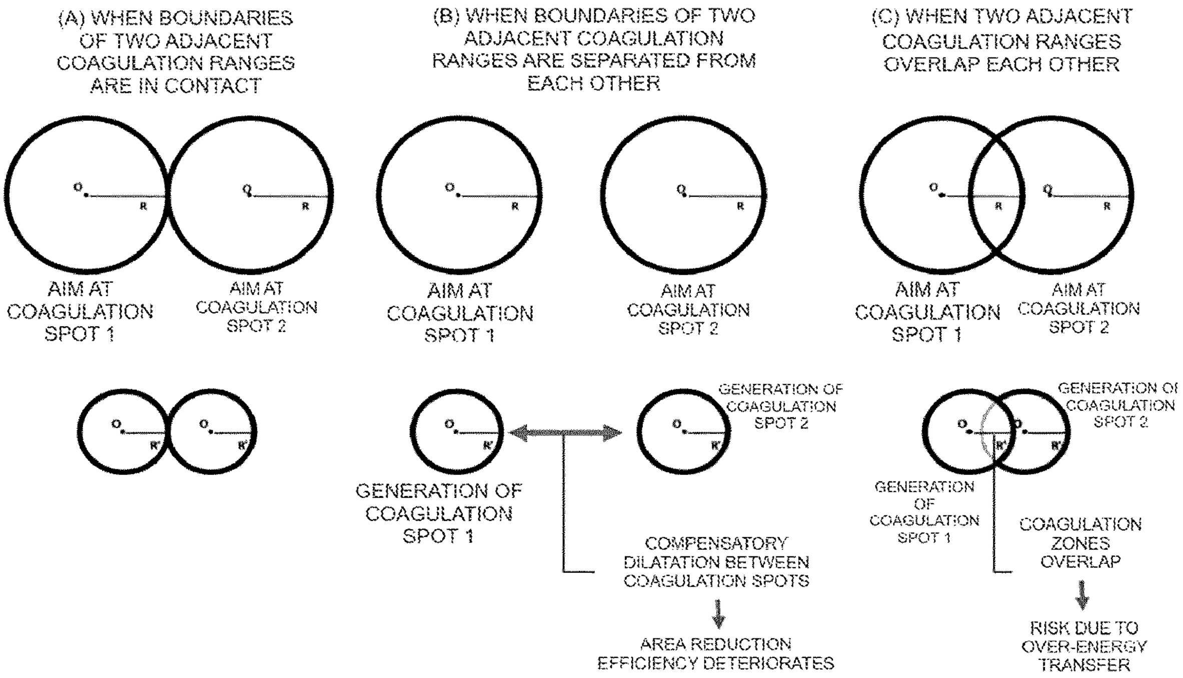

FIGS. 5 and 6 describe that safety and area reduction efficiency may vary depending on the distance between adjacent coagulation spots when reducing the area of the skin by generating several coagulation spots.

Referring to FIGS. 5 and 6, when coagulation ranges are not in contact with each other and are separated from each other, non-coagulated skin therebetween increases (compensatory dilatation), and thus the overall area reduction effect is reduced. Conversely, when overlapping between coagulation zones occurs, there is a risk that temperature may excessively rise (for example, about 80 degrees Celsius or more) and covalent bonds inside collagen molecules may be broken down, causing dissolution thereof.

Figure 7:
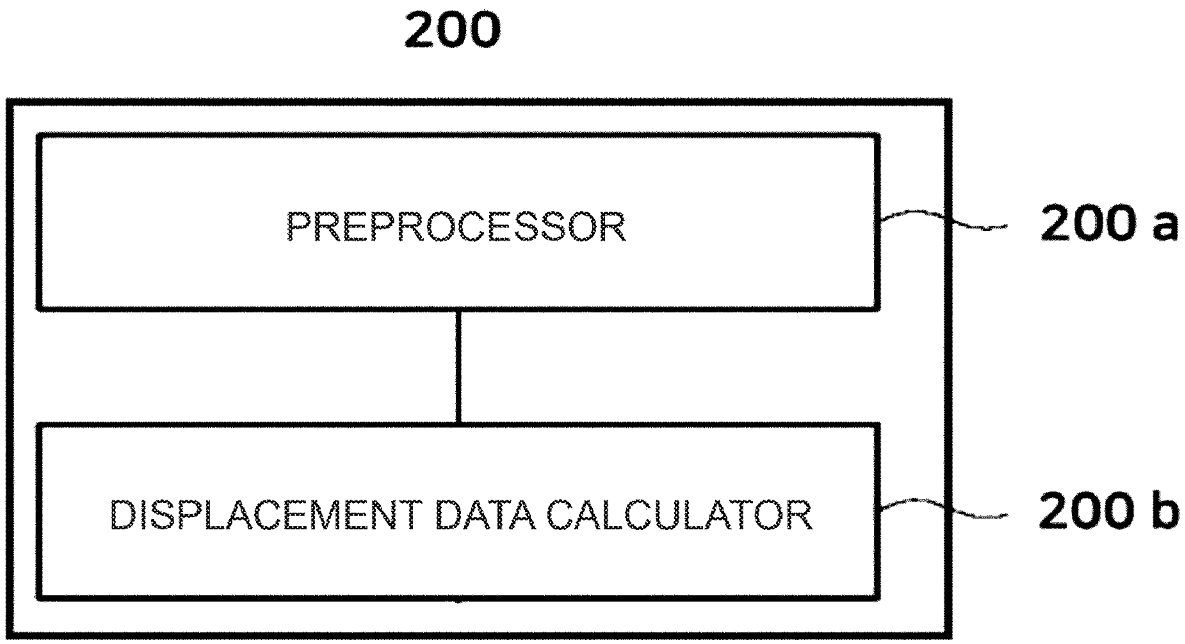
FIGS. 7 and 8 are a configuration diagram of a displacement calculator 200 and a process diagram of calculating location data by a preprocessor 200*a* according to an embodiment of the present invention.
Figure 8:
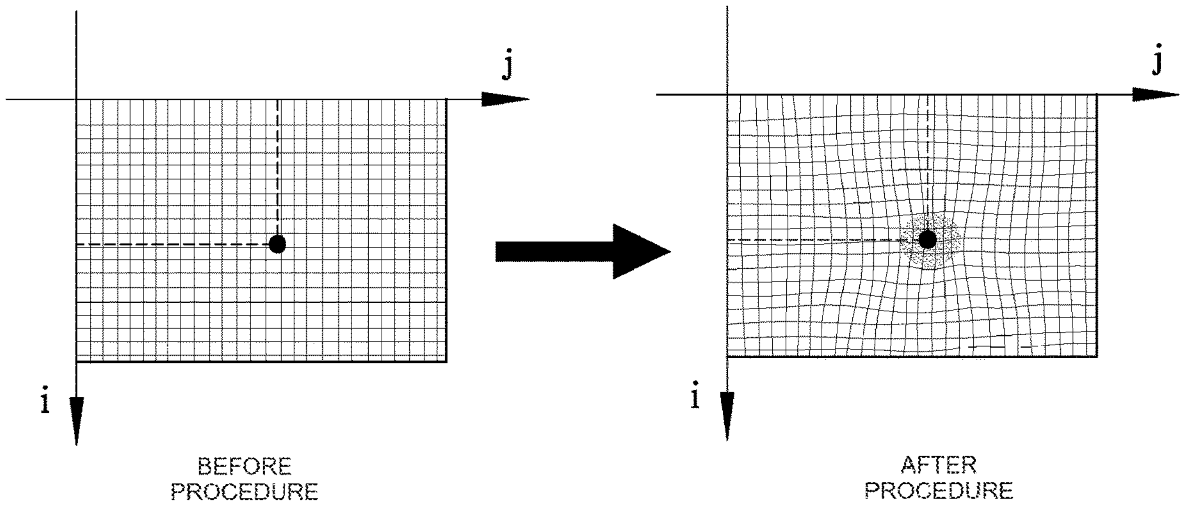

FIGS. 7 and 8 are a configuration diagram of the displacement calculator 200 and a process diagram of calculating location data by a preprocessor 200*a* according to an embodiment of the present invention.

Referring to FIG. 7, the displacement calculator 200 includes the preprocessor 200*a* and a displacement data calculator 200*b*. The preprocessor 200*a* converts location data A of landmarks before the skin procedure on the skin surface in a captured skin surface image before the procedure into A[(i, j)ij], and converts location data B of landmarks after the skin procedure on the skin surface in a skin surface image after the procedure into B[(i', j')ij]. Further, the displacement data calculator 200*b* generates, as the landmark displacement data D, a displacement vector reflecting a result of movement from location data before the skin procedure to location data after the procedure based on the location data of the landmarks on the skin derived by the preprocessor 200*a*.

A more detailed description will be given with reference to FIG. 8. The preprocessor 200*a* calculates and stores location data A of landmarks on the skin surface before the skin procedure from the image captured before the skin procedure, and calculates and stores location data B of landmarks on the skin surface after the skin procedure from the image captured after the skin procedure according to movement of locations of the landmarks on the skin surface before the skin procedure to the contraction center O due to the skin procedure. Thereafter, the location data A of the landmarks on the skin surface before the skin procedure is represented as A[(i, j)ij], and the location data B of the landmarks on the skin surface after the skin procedure is represented as B[(i', j')ij]. That is, in more detail, as an embodiment of the present invention, in order to calculate each of the location data A of the landmarks on the skin surface before the skin procedure and the location data B of the landmarks on the skin surface after the skin procedure, pixel coordinates in the captured images before and after the skin procedure are expressed in a 2D Cartesian coordinate system having the origin at a top left vertex of the images, an i-axis directed downward along a vertical line, and a j-axis directed rightward along a horizontal line, and represented by the following matrix A in which coordinates (i, j) of each pixel on the image data correspond to an element in a row i and a column j.

$$A = \begin{bmatrix} (1,1) & (1,2) & (1,3) & \\ (2,1) & (2,2) & (2,3) & \cdots \\ (3,1) & (3,2) & (3,3) & \\ & \vdots & & \ddots \end{bmatrix}$$

The location data B of the landmarks on the skin surface after the skin procedure may be represented by a matrix [(i', j')ij] having, as an element, coordinates (i', j') of a point at which each element [(i, j)ij] of the matrix A arrives after contraction.

Figure 9:
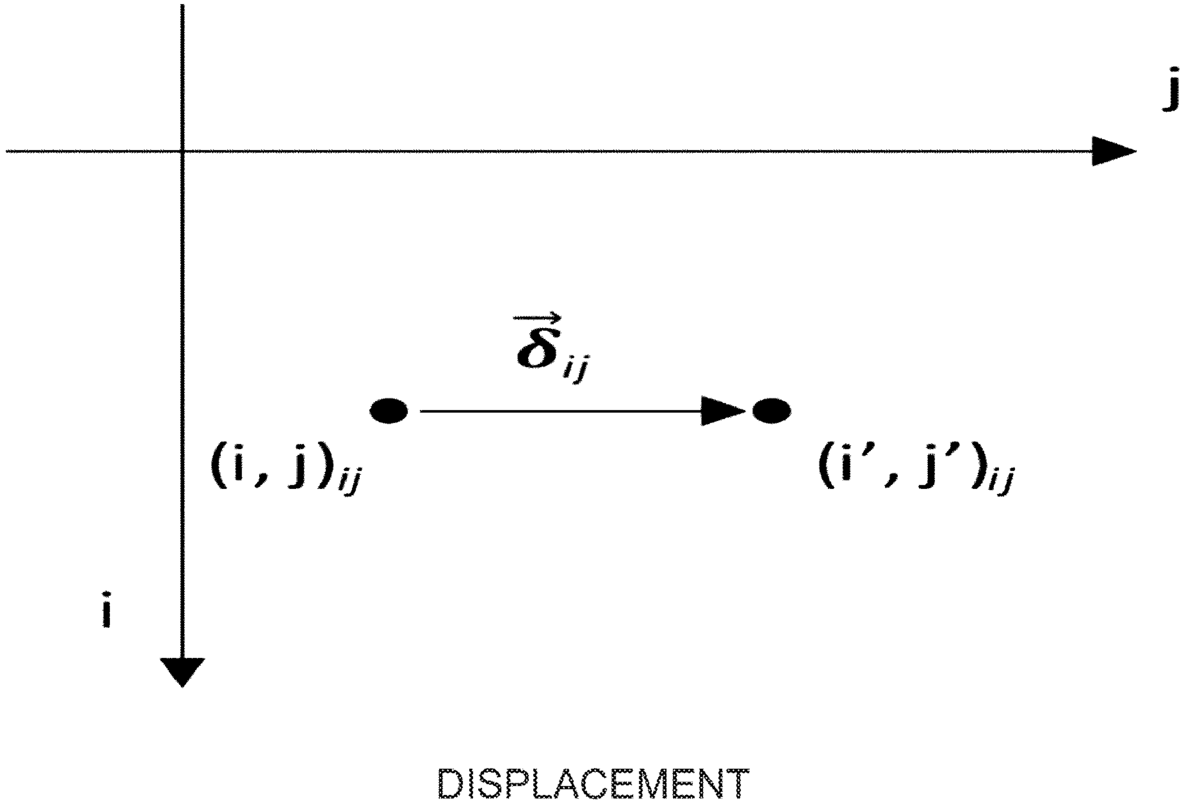
FIG. 9 is a process diagram of calculating displacement data D by a displacement data calculator 200*b* according to an embodiment of the present invention.

FIG. 9 is a state of calculating the displacement data D by the displacement data calculator 200*b* according to an embodiment of the present invention.

Referring to FIG. 9, the displacement data calculator 200*b* represents the landmark displacement data D as [(i'-i, j'-j)ij]. That is, in more detail, the displacement data calculator 200*b* represents a result obtained by movement of the location data of the skin landmarks derived by the preprocessor from the location data A before the skin procedure to the location data after the procedure by displacement data D expressed as a vector $\vec{\delta}$ij. Here, as an example of the displacement data D, D=[(i'-i, j'-j)ij]=[$\vec{\delta}$ij].

(Here, i' and j' are a row i' and a column j' of B[(i', j')ij], and i and j are a row i and a column j of A[(i, j)ij].

Figure 10:
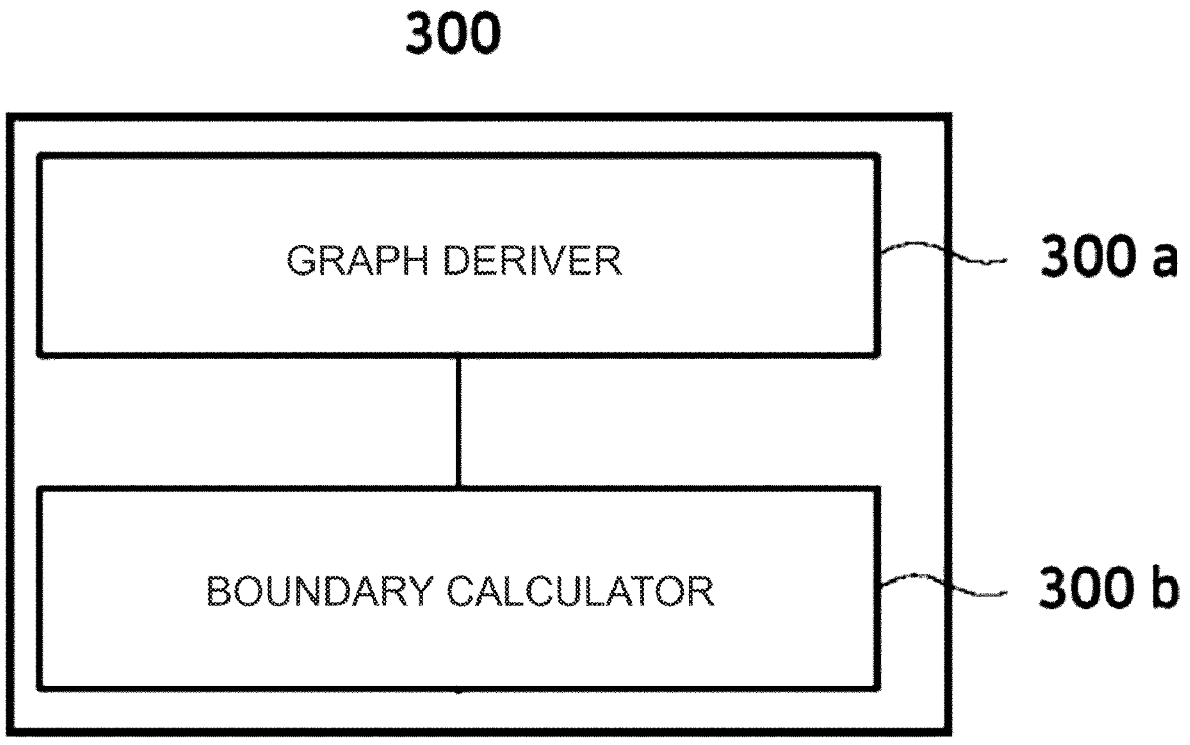
FIG. 10 is a configuration diagram of a boundary deriver 300 according to an embodiment of the present invention.

FIG. 10 is a configuration diagram of the boundary deriver 300 according to an embodiment of the present invention.

Referring to FIG. 10, the boundary deriver 300 includes a graph deriver 300*a* and a boundary deriver 300*b*. Here, the graph deriver 300*a* derives a displacement graph of each point moving toward the contraction center O for each location on a straight line passing, at an angle ⊖, through the contraction center O corresponding to a location of a focus to which the energy-based medical device applies energy based on the landmark displacement data, and the boundary deriver 300*b* calculates the distance R from the contraction center O to the contraction zone boundary based on graph analysis result data derived by the graph deriver 300*a*.

Figure 11:
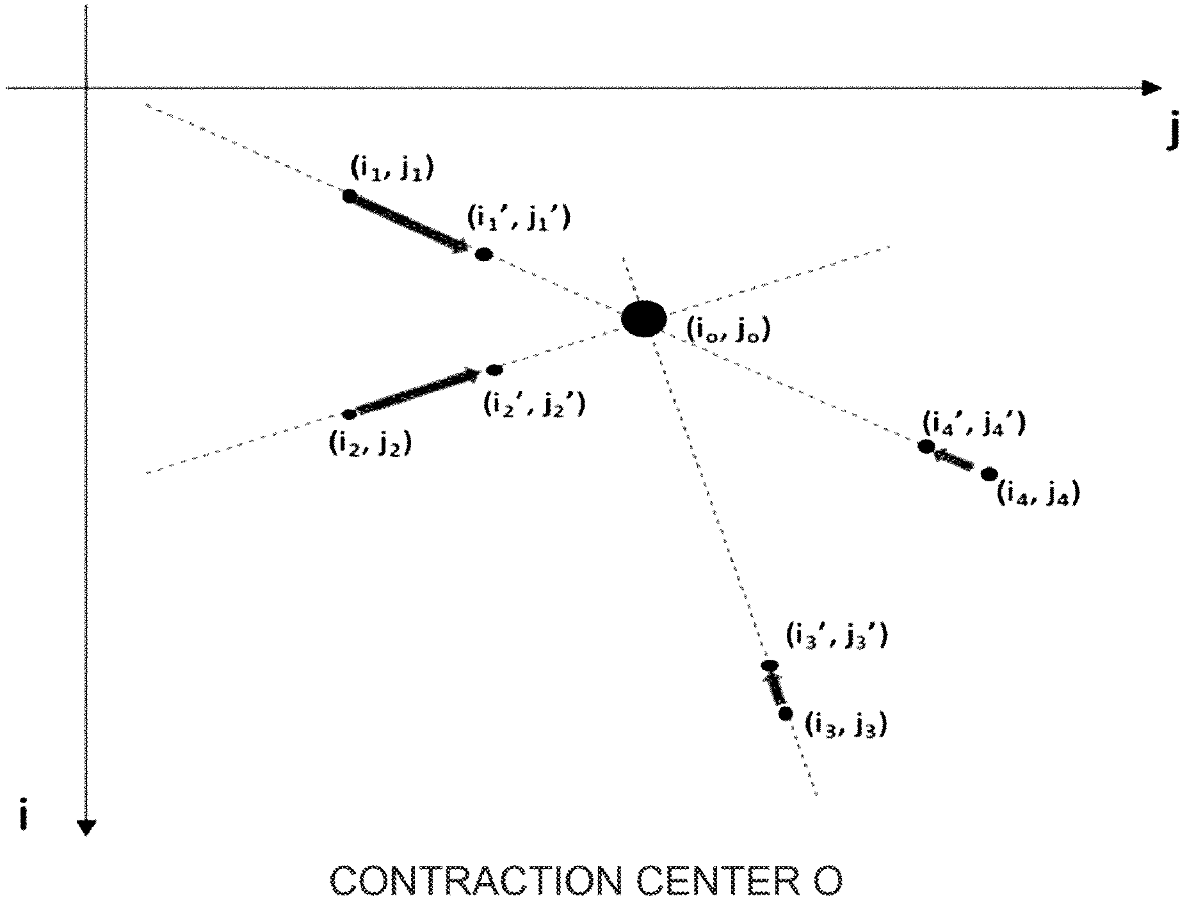
FIG. 11 is a process diagram of calculating a location of a contraction center O by a graph deriver 300*a* according to an embodiment of the present invention.

FIG. 11 is process of calculating a location of the contraction center O by the graph deriver 300*a* according to an embodiment of the present invention.

Referring to FIG. 11, the graph deriver 300*a* may calculate location data of the contraction center O based on the location data A before the procedure and the displacement data D even when the location of the contraction center O is not known. That is, in more detail, the graph deriver 300*a* sets the location data of the contraction center O corresponding to a location of a focus to which the energy-based medical device applies energy based on the landmark displacement data D, the location data of the contraction center O is a location of a point to which landmark points on the skin surface are commonly directed during skin coagulation according to the procedure, and a location of an intersection point of straight lines, which are obtained by points corresponding to the respective elements (i, j)ij of the location data A of the landmarks on the skin surface before the skin procedure each directed in a direction of an element $\vec{\delta}$ij vector of the landmark displacement data D, is set to (io, jo).

Figure 12:
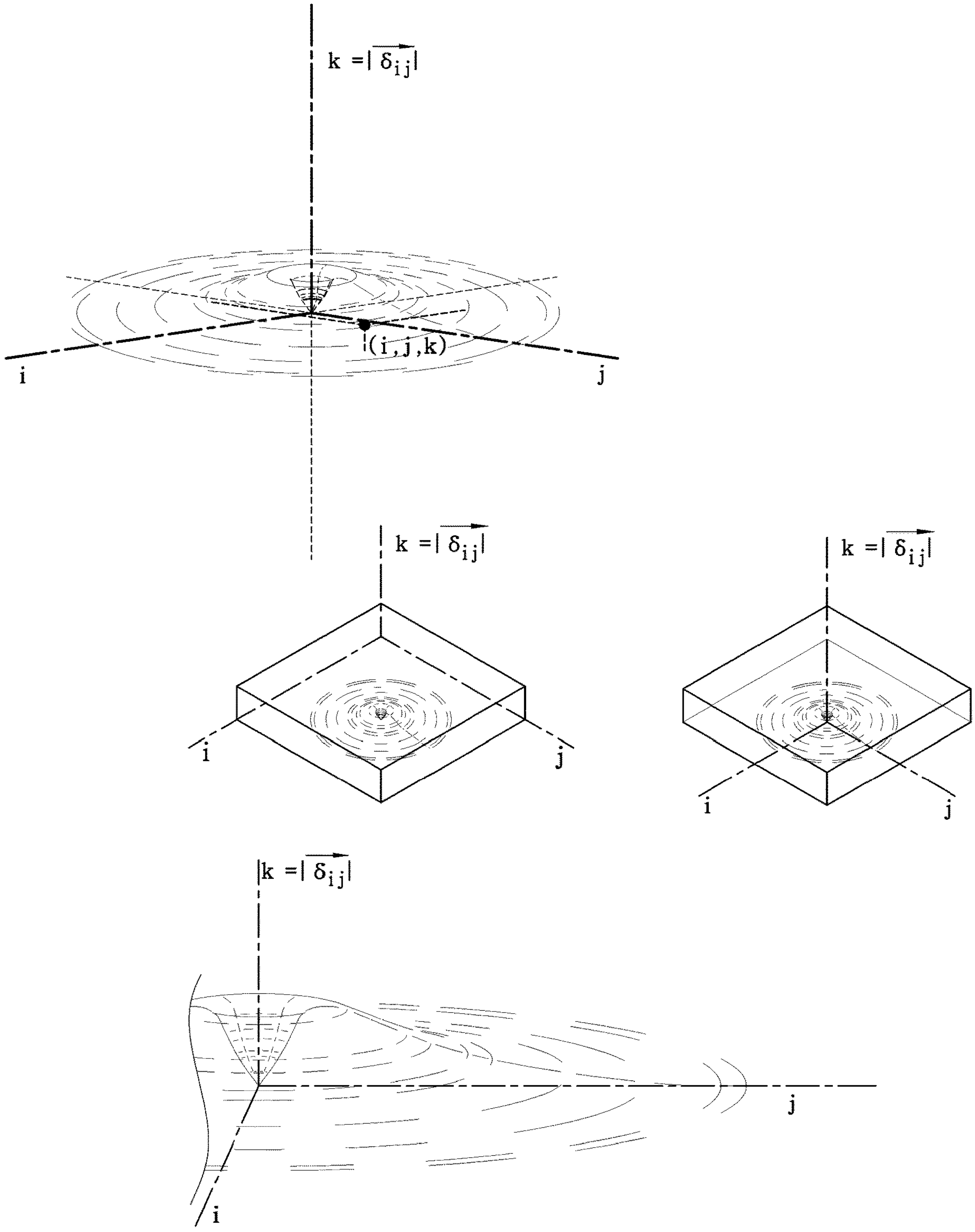
FIG. 12 is a graph of the graph deriver 300*a* according to an embodiment of the present invention.

FIG. 12 is a graph of the graph deriver 300*a* according to an embodiment of the present invention.

Referring to FIG. 12, the graph deriver 300*a* may derive a graph of a distance (displacement) of each point moving toward the contraction center O for each point on a straight line passing through the contraction center O at a desired angle ⊖ in the captured image before the procedure using the location data and the displacement data as input.

According to optimal embodiments of the present invention, the graph deriver 300*a* derives a displacement graph after the procedure with respect to a distance of each of landmarks on a straight line, which passes through the contraction center O in the skin procedure at the desired angle ⊖, from the contraction center O before the procedure, performs parallel translation by -io on the i-axis and -jo on the j-axis with respect to the contraction center O (io, jo, 0) in the skin procedure, and performs rotation by the angle ⊖ at which the contraction center O in the skin procedure is passed through on a k-axis, thereby deriving a graph of k with respect to i in an ik-plane (j=0). That is, in more detail, in a three-dimensional (3D) Cartesian coordinate system obtained by adding the k-axis to the Cartesian coordinate system of the i-axis and the j-axis, a set of points [i, j, |$\vec{\delta}$ij|] where values corresponding to the i-axis and the j-axis are set to values i and j of an element [(i, j)ij] of the matrix A, and a value corresponding to the k-axis is set to the magnitude |$\vec{\delta}$ij| of a vector element of the data D corresponding to the element [(i, j)ij] of matrix A, may be represented by a graph, which may be moved by -io on the i-axis and -jo on the j-axis to place a center of symmetry thereof on the k-axis, then rotated by the angle ⊖ around the k-axis, and then expressed as a graph of k with respect to i in the ik-plane (j=0). In the process of deriving a graph, a location of a coagulation center O is not given, and a description has been given of a method capable of calculating a displacement distribution graph for all straight lines passing through the unknown coagulation center O. However, when the location of the coagulation center O is previously known, or only a displacement graph on one straight line is to be obtained, the corresponding step in the process of deriving a graph may be omitted.

Figure 13:
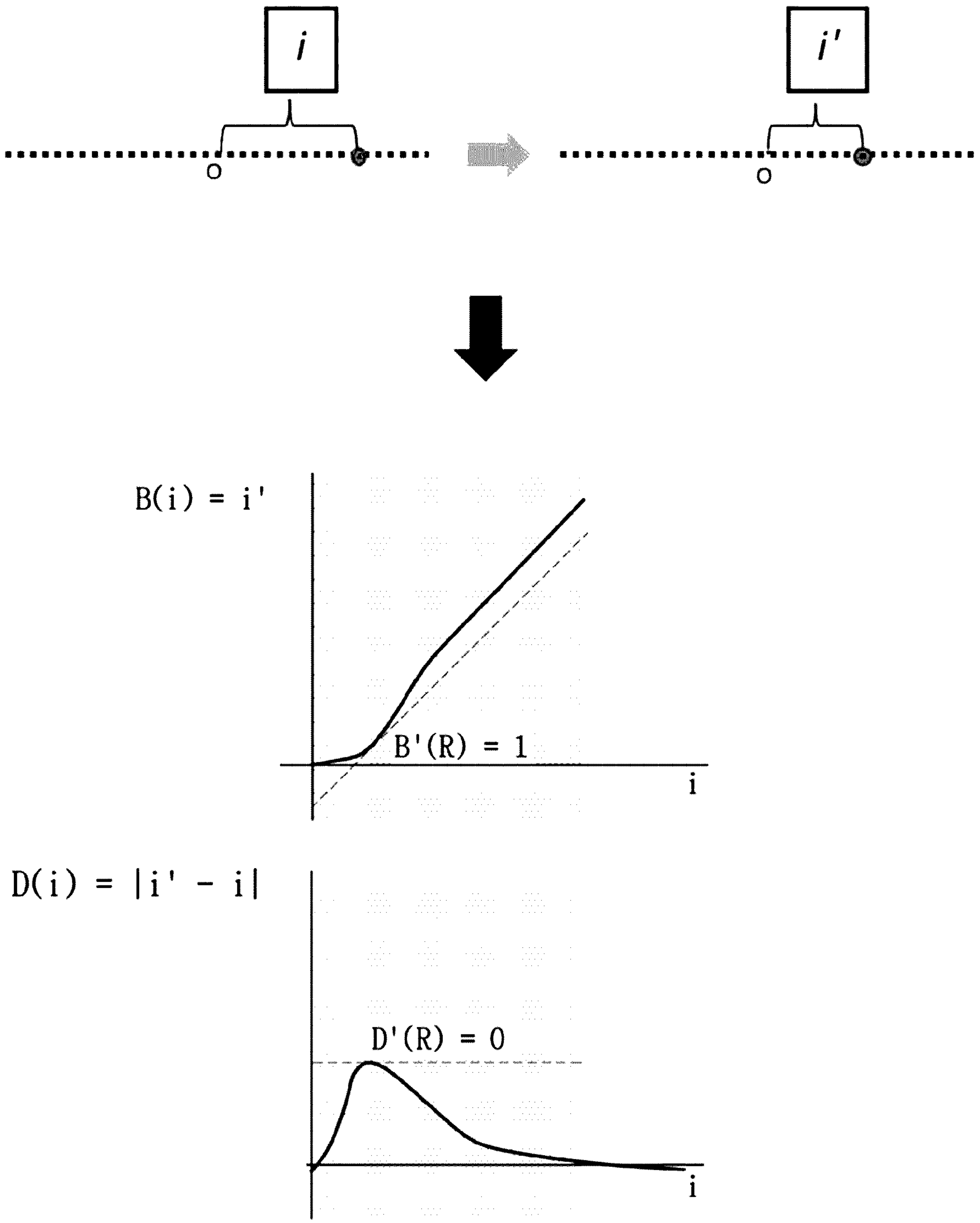
FIG. 13 is a process diagram of calculating a size and shape of a coagulation center contraction zone by a boundary deriver 300*b* according to an embodiment of the present invention.

FIG. 13 is a process of calculating a size and shape of the coagulation center contraction zone by the boundary deriver 300*b* according to an embodiment of the present invention.

Referring to FIG. 13, the boundary deriver 300*b* derives a graph of a regression curve of a distance by which each point moves toward the contraction center O in the skin procedure for each location on the horizontal line (⊖=0) passing through the contraction center O in the skin procedure, and calculates a distance from the contraction center O to the boundary R of the contraction zone from the captured image before the procedure based on the fact that the distance is close to a distance from the contraction center O to a point where a slope of a tangent becomes 0 on the regression curve. Therefore, it is possible to derive a regression curve for a scatter plot including discrete values obtained from actual observations.

As an embodiment of the present invention, the graph of the distance (displacement) by which each point moves toward the contraction center O for each point on the straight line passing through the contraction center O at the desired angle ⊖ in the captured image before the procedure obtained by the graph deriver 300*a* regresses to a distribution curve D(i) having positive numbers as elements (Lognormal distribution, Chi-square distribution, F-distribution, and other distribution curves having positive numbers as elements). Thus, with respect to a distance (i) from the contraction center O to an element of the location data A before the procedure derived by the preprocessor 100, a graph of a distance (i') to an element of the location data B after the procedure corresponding to the element may be represented by B(i)=i-D(i). Therefore, the boundary deriver 300*b* may derive a size and shape of the contraction zone based on the fact that an i-coordinate at a point where a slope B' (i) of a tangent is 1 is close to a distance from the contraction center O to the boundary R of the contraction zone in the same direction on the curve B(i). Here, the graph of the distance (i') to the element of the location data B after the procedure corresponding to the element of the location data A before the procedure with respect to the distance (i) from the contraction center O to the element of the location data A before the procedure derived by the preprocessor 100 regresses to the curve B(i).

Further, in an embodiment of the present invention, when a cross section of the displacement graph derived by the graph deriver 300*a* regresses to a distribution curve having positive numbers as elements, the boundary deriver 300*b* may calculate the size and shape of the contraction zone based on the fact that a mode of the distribution, that is, an i-coordinate at a highest point where a slope of a tangent is 0 is close to a distance from the contraction center O to the boundary R of the contraction zone on a straight line passing through the contraction center O at an angle corresponding to the cross section. Since the distance from the contraction center O to the boundary R of the contraction zone may vary depending on the direction of the straight line passing through the contraction center O, the 3D graph derived by the graph deriver 300*a* may be rotated by a desired angle around the contraction center O to cause the boundary deriver 300*b* to calculate a distance to the boundary R of the contraction zone in all directions with respect to the contraction center O, which corresponds to obtaining the size and shape of the contraction zone.

Figure 14:
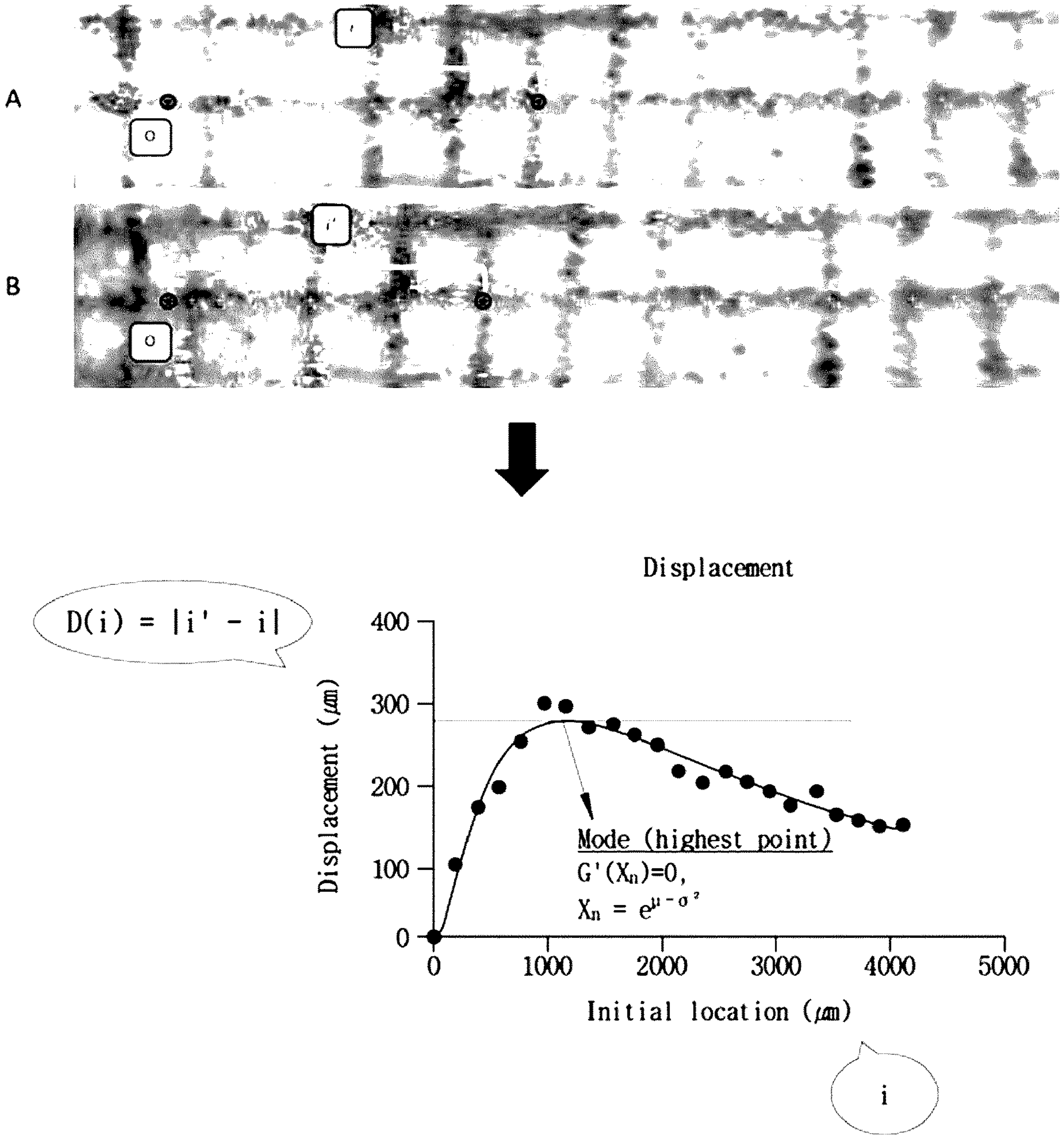
FIG. 14 is a calculation process diagram when an angle of a straight line passing through a contraction center is 0 (⊖=0) according to an embodiment of the present invention.

FIG. 14 is a calculation process when an angle of a straight line passing through a contraction center is 0 (θ=0) according to an embodiment of the present invention. Referring to FIG. 14, the location data A before the procedure and the location data B after the procedure may be obtained based on landmark location data preprocessed by the preprocessor 100. Thereafter, the displacement calculator 200 calculates displacement D(i), which is a change in location data for each coagulation point of the skin, based on the location data acquired by the preprocessor 100. The location of the contraction center O is previously known or is obtained through calculation by the displacement calculator 200 as described in the embodiment of the graph deriver 300*a*, and then a graph is derived by the graph deriver 300*a* through this value. A cross section of a graph moved to the origin of a virtual coordinate system to calculate the size and shape of the contraction zone by the boundary deriver 300*b* regresses to a lognormal distribution with a regression coefficient of 0.6 or more ($R^2$=0.9562). Therefore, it may be determined that the scatter plot is not different from a population following the lognormal distribution of $$D(i) = \frac{1}{i\sigma\sqrt{2\pi}}e^{\left\{-\frac{(ln\,i-\mu)^2}{2\sigma^2}\right\}}.$$

In the regressing displacement distribution curve D(i), a highest point corresponds to a mode, and a slope D'(i) of a tangent at the point is 0. In the lognormal distribution, a mode is $e^{\mu-\sigma^2}$ (e being a natural constant, μ being a mean, and σ being a standard deviation), and thus a value i and a value i' satisfying D'(i)=0 may be obtained by a probability density function equation. Therefore, by providing information on the shape and size of the contraction zone derived through the boundary deriver 300 to the operator or device, it is possible to implement an optimal state illustrated in the drawings of FIGS. 5 and 6, that is, a state in which boundaries of the contraction zones are in contact.

Figure 15:
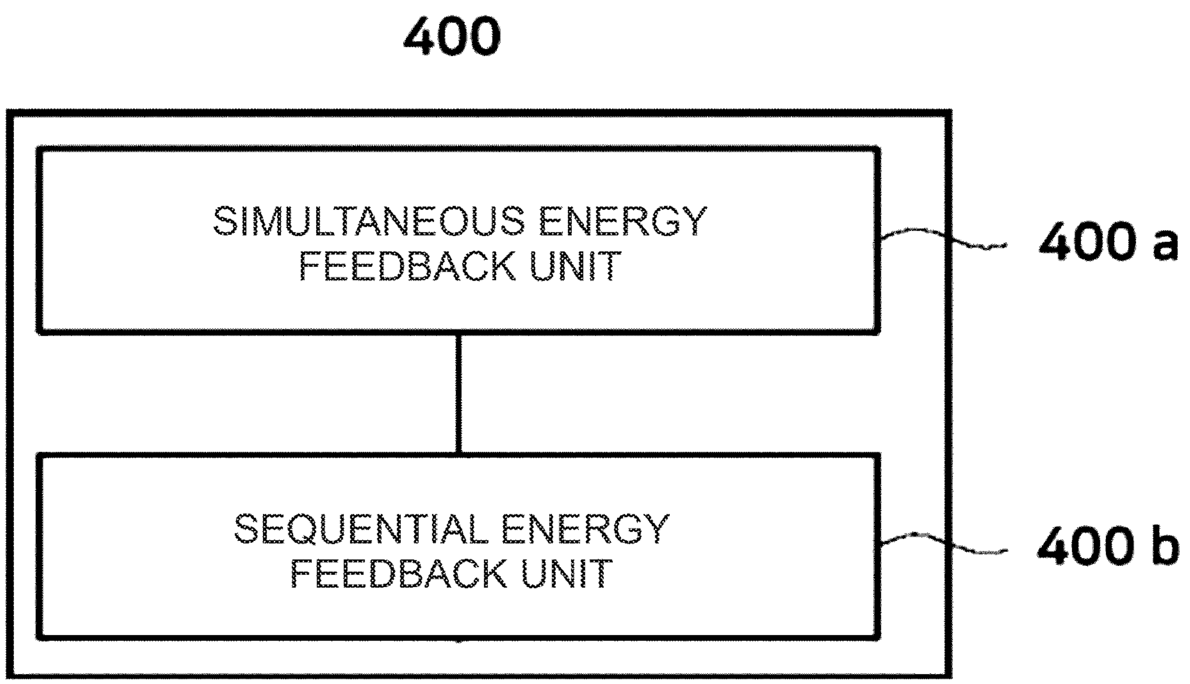
FIG. 15 is a configuration diagram of a procedure feedback unit 400 according to an embodiment of the present invention.

FIG. 15 is a configuration diagram of the procedure feedback unit 400 according to an embodiment of the present invention.

Referring to FIG. 15, the procedure feedback unit 400 includes a simultaneous energy feedback unit 400*a* and a sequential energy feedback unit 400*b*.

When coagulation spots are simultaneously generated through the energy-based medical device (simultaneous model), the simultaneous energy feedback unit 400*a* feeds back a minimum distance D preventing coagulation zones from overlapping each other. As an embodiment of the present invention, when a size of the contraction zone derived by the boundary deriver 300 is smaller than a fixed procedure distance of the energy-based medical device, the simultaneous energy feedback unit 400*a* feeds back high output energy value information to the energy-based medical device so that output of the energy-based medical device may be increased. Conversely, when the size of the contraction zone derived by the boundary deriver 300 is greater than the fixed procedure distance of the energy-based medical device, low output energy value information is fed back to the energy-based medical device so that output of the energy-based medical device may be decreased.

That is, in more detail, the simultaneous energy feedback unit 400*a* causes the energy-based medical device that promotes skin area contraction to generate several coagulation spots on the skin. Here, a type in which a plurality of coagulation spots is simultaneously generated is referred to as a simultaneous model. In the case of the simultaneous model, based on a calculation system of the present invention, a device capable of freely adjusting a distance between coagulation spots performs feedback so that output is increased when contraction zones are excessively small, and thus contraction zones are excessively far apart even when a distance between coagulation spots is minimized to an implementable distance, and conversely performs feedback so that output is decreased when contraction zones are excessively large, and thus contraction zones overlap each other even when the distance is maximized.

In addition, in the case of the simultaneous model, a device in which a distance between coagulation spots is fixed (or a device including discontinuous values for each step) performs feedback so that output is further increased when sizes of generated contraction zones are excessively small as a result of calculation, and thus a distance between boundaries is excessively large even in the case of an implementable minimum distance, and conversely performs feedback so that output is further decreased when contraction zones are excessively large, and thus it is determined that contraction zones overlap each other when several contraction zones are generated at a current interval.

Finally, in the case of a device in which a distance is adjusted to discontinuous values such as step 1/step 2/step 3, etc., feedback may be performed to increase or decrease the step of the distance or to decrease or increase the output.

When coagulation spots of the skin are sequentially generated through the energy-based medical device (sequential model), the sequential energy feedback unit 400*b* feeds back a minimum distance D' that prevents coagulation zones in (N−1)th to Nth rounds from overlapping, and feeds back a location of a coagulation spot to be generated in the Nth round based on the displacement graph derived by the boundary deriver 300 and information on a size and shape of a contraction zone based on one coagulation spot generated in the (N−1)th round. That is, in more detail, a type in which a plurality of coagulation spots is simultaneously generated is referred to as a simultaneous model, and in the case of the simultaneous model, a preferable location of a coagulation spot to be generated in an (N+1)th round is fed back based on a displacement graph obtained as a result of calculation based on a skin contraction aspect caused by one coagulation spot generated in the Nth round and information on a size and shape of a contraction zone.

According to the device factor calculation system based on skin surface displacement described above, there are the following effects. According to the device factor calculation system based on skin surface displacement described above, there are the following effects. First, it is possible to derive displacement of each point on a skin surface that contracts when one focal point on the skin is treated using an energy-based medical device. Second, it is possible to derive a location of a contraction center caused by the procedure based on photographs taken before and after the procedure. Third, it is possible to quantitatively express an aspect of skin contraction by the procedure based on the derived data. Fourth, it is possible to quantitatively express an aspect of skin contraction, which varies according to a patient undergoing the procedure and a part thereof and according to a type and output of the device, whenever the system is applied. Fifth, it is possible to generate data necessary for deriving an optimal next procedure location or procedure output during the procedure based on mathematical calculation rather than intuition of the operator. Sixth, it is possible to combine distribution information on a contraction aspect of skin in several parts in one procedure target to calculate and propose a 2D arrangement and order of several procedure points for realizing a change to desired appearance through manipulation of a location of each point on the skin.

Even though the detailed description of the present invention described above has been given with reference to preferred embodiments of the present invention, those skilled in the art or those having ordinary knowledge in the art may understand that the present invention may be variously modified and changed within the scope not departing from the spirit and technical scope of the present invention described in the claims to be described later.

INDUSTRIAL APPLICABILITY

The device factor calculation system based on skin surface displacement may be installed in various energy-based medical devices such as fractional fine needle radiofrequency, fractional laser, and high-intensity focused ultrasound devices, and cosmetic effects may be maximized through automatic calculation of contraction of a skin plane and a calculated value.

The invention claimed is:

1. A skin procedure guidance and feedback system, comprising:

- a photographing unit configured to photograph skin before and after a procedure by an energy-based medical device;
- a displacement calculator configured to derive landmark displacement data from landmark location data of the skin photographed by the photographing unit; and
- a procedure feedback unit configured to feed back optimal parameter information for the procedure based on the landmark displacement data,
- wherein the optimal parameter information comprises locations of coagulation spots generated by the energy-based medical device, an arrangement of the coagulation spots, and an output of the energy-based medical device.

2. The skin procedure guidance and feedback system according to claim 1, wherein the energy-based medical device is configured to:

- apply energy to one focus of the skin to cause a local temperature rise, thereby generating a contraction zone based on the one focus of the skin; and
- include high-frequency, laser, and high-intensity focused ultrasound (HIFU) devices.

3. The skin procedure guidance and feedback system according to claim 1, wherein the photographing unit is configured to photograph a skin surface before the procedure and a skin surface after the procedure based on the energy-based medical device.

4. The skin procedure guidance and feedback system according to claim 1, wherein landmarks of the skin comprise dots or lines marked with pigment, sweat glands, hair glands, sebaceous glands, pigmented lesions, moles, skin tumors, blood vessels, and wrinkle lines on a skin surface as reference points enabling tracking of positional change of a skin procedure target part before and after the procedure in photographed images taken before and after the procedure through the energy-based medical device.

5. The skin procedure guidance and feedback system according to claim 1, wherein the displacement calculator comprises:

a preprocessor configured to collect location data of landmarks before the procedure on a skin surface in an image of the skin surface before the procedure and location data of landmarks after the procedure on the skin surface in an image of the skin surface after the procedure; and a displacement data calculator configured to calculate, as the landmark displacement data, a displacement vector reflecting a result of movement from the location data before the procedure to the location data after the procedure based on the landmark location data of the skin derived by the preprocessor.

6. The skin procedure guidance and feedback system according to claim 5, wherein the displacement data calculator is configured to:

derive the landmark displacement data by comparing the location data of the landmarks before the procedure and the location data of the landmarks after the procedure.

7. The skin procedure guidance and feedback system according to claim 1, wherein the displacement calculator is configured to to derive location data of a contraction center based on the landmark displacement data.

8. The skin procedure guidance and feedback system according to claim 7, further comprises:

a boundary deriver configured to derive a boundary of a contraction zone from the contraction center in the procedure.

9. The skin procedure guidance and feedback system according to claim 8, wherein the boundary deriver comprises:

a graph deriver configured to derive a displacement graph of the landmark displacement data; and a boundary calculator configured to calculate a distance from the contraction center to the boundary of the contraction zone based on graph analysis result data derived by the graph deriver.

10. The skin procedure guidance and feedback system according to claim 9, wherein the boundary deriver is configured to:

derive a graph representing a magnitude of displacement vectors of each landmark according to positions of the displacement vectors.

11. The skin procedure guidance and feedback system according to claim 10, wherein the boundary deriver is configured to:

derive the graph representing the magnitude of the displacement vectors of the each landmark according to the positions of the displacement vectors based on a direction of the displacement vectors relative to the contraction center.

12. The skin procedure guidance and feedback system according to claim 9, wherein the boundary deriver is configured to:

derive a graph of a regression curve based on the landmark displacement data; and calculate the distance from the contraction center to the boundary of the contraction zone from a captured image before the procedure based on a fact that the distance is close to a distance from the contraction center to a point where a slope of a tangent becomes 0 on the regression curve.

13. The skin procedure guidance and feedback system according to claim 8, wherein, when a size of the contraction zone derived by the boundary deriver is smaller than a distance between adjacent coagulation spots on the arrangement of the coagulation spots of the energy-based medical device, the procedure feedback unit is configured to feed back high output energy value information to the energy-based medical device so that the output of the energy-based medical device is allowed to be increased.

14. The skin procedure guidance and feedback system according to claim 8, wherein, when a size of the contraction zone derived by the boundary deriver is greater than a distance between adjacent coagulation spots on the arrangement of the coagulation spots of the energy-based medical device, the procedure feedback unit is configured to feed back low output energy value information to the energy-based medical device so that the output of the energy-based medical device is allowed to be decreased.

15. The skin procedure guidance and feedback system according to claim 8, wherein, when a plurality of the coagulation spots are generated through the energy-based medical device, the procedure feedback unit is configured to feed back the locations of the coagulation spots to prevent coagulation zones from overlapping each other.

16. The skin procedure guidance and feedback system according to claim 15, wherein, when the plurality of the coagulation spots on the skin are sequentially generated through the energy-based medical device, the procedure feedback unit is configured to feed back a minimum distance between adjacent coagulation spots to prevent the coagulation zones formed by the energy-based medical device from overlapping each other based on sizes and shapes before and after contraction of a plurality of contraction zones derived by the boundary deriver.

17. The skin procedure guidance and feedback system according to claim 15, wherein, when the plurality of the coagulation spots on the skin are simultaneously generated through the energy-based medical device, the procedure feedback unit is configured to feed back a minimum distance between adjacent coagulation spots on the arrangement to prevent the coagulation zones formed by the energy-based medical device from overlapping each other based on sizes and shapes after contraction of a plurality of contraction zones derived by the boundary deriver.

18. The skin procedure guidance and feedback system according to claim 1, wherein, when a plurality of the coagulation spots are generated through the energy-based medical device, the procedure feedback unit is configured to feed back the output of the energy-based medical device to prevent coagulation zones from overlapping each other.

* * * * *